(12) United States Patent
Boukhayma et al.

(10) Patent No.: US 9,462,198 B2
(45) Date of Patent: Oct. 4, 2016

(54) IMAGE ACQUISITION METHOD AND SYSTEM

(71) Applicant: Commissariat à L'énergie Atomique et aux énergies Alternatives, Paris (FR)

(72) Inventors: Assim Boukhayma, Grenoble (FR); Antoine Dupret, Orsay (FR)

(73) Assignee: Commissariat a l'energie atomique et aux energies alternatives (FR)

( * ) Notice: Subject to any disclaimer, the term of this patent is extended or adjusted under 35 U.S.C. 154(b) by 384 days.

(21) Appl. No.: 14/196,794

(22) Filed: Mar. 4, 2014

(65) Prior Publication Data

US 2014/0253734 A1    Sep. 11, 2014

(30) Foreign Application Priority Data

Mar. 5, 2013  (FR) ...................................... 13 51922

(51) Int. Cl.

| | |
|---|---|
| *G01N 21/35* | (2014.01) |
| *H04N 5/30* | (2006.01) |
| *G01N 21/3586* | (2014.01) |
| *G01N 21/3581* | (2014.01) |
| *G01S 17/89* | (2006.01) |

(52) U.S. Cl.
CPC ............ *H04N 5/30* (2013.01); *G01N 21/3581* (2013.01); *G01N 21/3586* (2013.01); *G01S 17/89* (2013.01)

(58) Field of Classification Search
CPC ...................... G01N 21/3581; G01N 21/3586
See application file for complete search history.

(56) References Cited

U.S. PATENT DOCUMENTS

| | | | | |
|---|---|---|---|---|
| 4,725,881 | A * | 2/1988 | Buchwald ............. | H04N 9/045 348/237 |
| 2002/0139920 | A1* | 10/2002 | Seibel .................. | A61B 1/0008 250/208.1 |
| 2006/0146340 | A1* | 7/2006 | Szwaykowski .... | G01B 9/02081 356/495 |
| 2007/0045685 | A1* | 3/2007 | Yang ................. | H01L 27/14621 257/294 |

(Continued)

FOREIGN PATENT DOCUMENTS

| | | |
|---|---|---|
| GB | 2458802 | 10/2009 |
| WO | 2005112130 | 11/2005 |

OTHER PUBLICATIONS

"Priority Application No. FR 13/51922 Search Report", Dec. 4, 2013, Publisher: inpi, Published in: FR.

(Continued)

*Primary Examiner* — Casey Bryant
(74) *Attorney, Agent, or Firm* — Kaplan Breyer Schwarz & Ottesen, LLP

(57) ABSTRACT

A method of acquiring an image of a scene illuminated by a first beam, by means of a sensor including at least two pixels, including the steps of: a) for each pixel, reading a first output value of the pixel representative of the intensity of the radiation received by the pixel during a first integration period during which the sensor is illuminated by a second beam coherent with the first beam; and b) for each pixel, reading a second output value of the pixel representative of the intensity of the radiation received by the pixel during a second integration period during which the sensor is not illuminated by the second beam, wherein steps a) and b) are repeated a plurality of times by changing, between two successive iterations, the angle of incidence or a phase parameter of the second beam.

11 Claims, 3 Drawing Sheets

(56) References Cited

U.S. PATENT DOCUMENTS

2011/0068272 A1* 3/2011 Dupont ............. G01J 5/20 250/338.4
2012/0211657 A1* 8/2012 Dupont ............. G01J 5/20 250/338.1

OTHER PUBLICATIONS

Schuster, et al., "ISSCC 2011 / Session 2 / Technologies for Health / A Broadband THz Imager in a Low-Cost CMOS", "Digest of Technical Papers", Feb. 21, 2011, Publisher: 2011 IEEE International Solid-State Circuits Conference, Published in: Grenoble, France.

Sherry, et al., "ISSCC 2012 / Session 15 / mm-Wave & THz Techniques / 15.1 / A 1kPixel CMOS Camera Chip for 25fps Real-Time Terahertz Imaging Applications", "Digest of Technical Papers", Feb. 21, 2012, Publisher: IEEE International Solid-State Circuits Conference, Published in: Crolles, FR.

Steinhauer, et al, "Millimeter-Wave-Radar Sensor Based on a Transceiver Array for Automotive Applications", "Transactions on Microwave Theory and Techniques", Feb. 2008, pp. 261-269, vol. 56, No. 2, Published in: DE.

Sengupta, et al., "Sub-THz Beam-forming using Near-field Coupling of Distributed Active Radiator Arrays", 2011, Publisher: Dept. of Electrical Engineering, California Institute of Technology, Pasadena, CA 91125, USA, Published in: US.

Lisauskas, et al., "Terahertz Detection and Coherent Imaging from 0.2 to 4.3 THz with Silicon CMOS Field-Effect Transistors", 2012, Publisher: Physikalisches Institut, Goethe-Universitt, D-60438 Frankfurt am Main, Germany, Published in: DE.

* cited by examiner

IMAGE ACQUISITION METHOD AND SYSTEM

This application claims the priority benefit of French patent application number 13/51922, filed on Mar. 5, 2013, the contents of which is hereby incorporated by reference in its entirety to the maximum extent allowable by law.

BACKGROUND

The present disclosure relates to image acquisition methods and systems.

DISCUSSION OF THE RELATED ART

So-called "active" image acquisition systems are known, which comprise:

an electromagnetic wave emission source arranged to illuminate or irradiate a scene to be observed; and an image sensor comprising an array of detectors or pixels sensitive to waves emitted by the source, arranged to receive the waves emitted by the source after reflection or transmission by transparency by the scene.

In an image acquisition phase, the scene is illuminated by the source, and the intensity of the radiation received by each sensor pixel is measured.

Active image acquisition methods and systems using sources emitting in terahertz or far infrared frequency ranges, for example, in the frequency range from 100 gigahertz (GHz) to 100 terahertz (THz), are more particularly considered herein.

An example of a laser spectrometer operating in the terahertz range is described in patent application GB2458802.

A problem which arises is due to the fact that detectors or pixels sensitive to terahertz or infrared waves have relatively large dimensions. Indeed, terahertz and infrared waves are characterized by wavelengths in the range from a few micrometers to a few millimeters, and the pixels should accordingly have dimensions of the same order. To limit their cost and/or to respect bulk constraints, terahertz or infrared image sensors thus generally have relatively low resolutions, which raises an issue when high-definition images are desired to be acquired.

SUMMARY

Thus, an embodiment provides a method of acquiring an image of a scene illuminated by a first electromagnetic wave beam, by means of a sensor comprising at least two pixels sensitive to said waves, comprising the steps of: a) for each pixel, reading a first output value of the pixel representative of the intensity of the radiation received by the pixel during a first integration period during which the sensor is illuminated by a second electromagnetic wave beam coherent with the first beam; and b) for each pixel, reading a second output value of the pixel representative of the intensity of the radiation received by the pixel during a second integration period during which the sensor is not illuminated by the second beam, wherein steps a) and b) are repeated a plurality of times by changing, between two successive iterations, the angle of incidence or a phase parameter of the second beam.

According to an embodiment, at each iteration, for each pixel of the sensor, a third value representative of the difference between the first and second output values of the pixel is calculated.

According to an embodiment, the sensor comprises an even number of pixels arranged in a circle, the pixels of the circle being distributed in pairs at diametrically opposite points of the circle.

According to an embodiment, at each iteration, for each pair of diametrically opposite pixels of the circle, a fourth value representative of the sum of the third values calculated for each of the pixels in the pair is calculated.

According to an embodiment, the second beam comprises first waves polarized along a first direction, and second waves polarized along a second direction different from the first direction.

According to an embodiment, the first and second directions are orthogonal.

According to an embodiment, at each iteration, a value of the phase shift between the first waves and the second waves is modified.

According to an embodiment, the electromagnetic waves are at a frequency in the range from 100 GHz to 100 THz.

According to an embodiment, the pixels are non-coherent pixels.

According to an embodiment, the second beam originates from a branching of the first beam.

Another embodiment provides a system for acquiring an image of a scene, comprising: a source emitting a first electro-magnetic wave beam capable of illuminating the scene; a sensor comprising at least two pixels sensitive to said waves; a source emitting a second electromagnetic wave beam coherent with the first beam capable of illuminating the sensor; and a control device capable of implementing the steps of: a) for each pixel, reading a first output value of the pixel representative of the intensity of the radiation received by the pixel during a first integration period during which the sensor is illuminated by the second beam; and b) for each pixel, reading a second output value of the pixel representative of the intensity of the radiation received by the pixel during a second integration period during which the sensor is not illuminated by the second beam, and repeating a plurality of times steps a) and b) by changing, between two successive iterations, the angle of incidence or a phase parameter of the second beam.

The foregoing and other features and advantages will be discussed in detail in the following non-limiting description of specific embodiments in connection with the accompanying drawings.

BRIEF DESCRIPTION OF THE DRAWINGS

For clarity, the same elements have been designated with the same reference numerals in the various drawings and, further, the various drawings are not to scale.

DETAILED DESCRIPTION

In an active terahertz or infrared image system, to obtain an image of the scene having a resolution greater than that of the sensor, it may be provided to mechanically displace the sensor with respect to the scene, to successively scan a plurality of portions of the scene. As an example, a partial image of the scene having a resolution equal to that of the sensor may be acquired at each step of the scanning, and the partial images may be combined to restore a full image of the scene having a resolution greater than that of the sensor. Such an image acquisition method however requires means of mechanical actuation of the sensor which may result being relatively complex.

Figure 1:
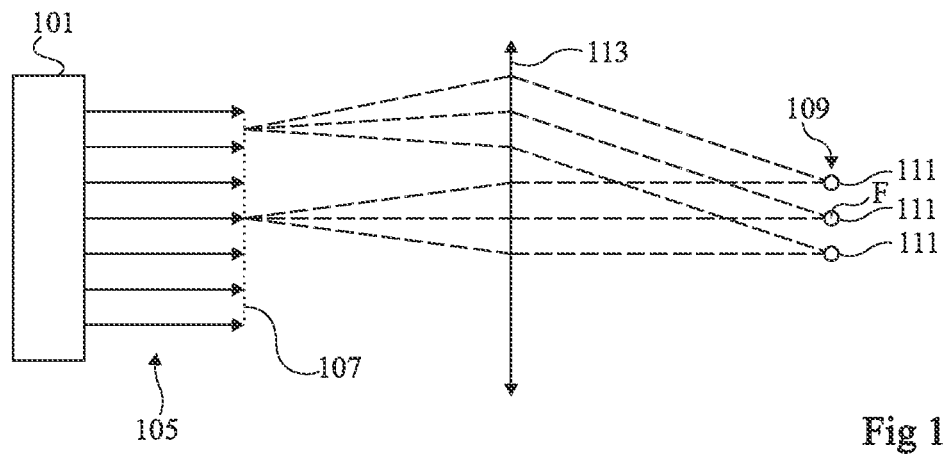
FIG. 1 is a cross-section view very schematically illustrating an example of an active image acquisition system.

FIG. 1 is a cross-section view schematically illustrating another example of an active image acquisition system enabling, without displacing the sensor, to obtain an image of a scene having a resolution greater than that of the sensor.

The system of FIG. 1 comprises a source 101 emitting coherent electromagnetic waves, for example, having a frequency in the range from 100 GHz to 100 THz. In this example, source 101 is capable of generating a parallel beam 105 of planar coherent waves capable of illuminating a scene or an object 107 to be observed. The system of FIG. 1 further comprises an image sensor 109 comprising a plurality of detectors or pixels 111 sensitive to the waves emitted by source 101. In the shown example, scene 107 to be observed is located between electromagnetic wave emission source 101 and sensor 109, the waves received by sensor 109 being transmitted through scene 107. In this example, the acquisition system comprises an optical system 113 arranged between scene 107 and sensor 109, capable of focusing the waves transmitted by scene 107 on sensor 109. Optical system 113 is such that the waves originating from each point in the scene to be observed are transmitted in a parallel beam, a planar wave, illuminating all the sensor pixels, the beam propagation direction depending on the position of the point on the scene. In other words, in the acquisition system of FIG. 1, the angle of incidence of the rays received by sensor 109 enables to discriminate waves originating from different points of the scene. To acquire an image of the scene, an angular filtering enabling the acquisition system to discriminate the signals received by the sensor by angles of incidence is used.

Figure 2:
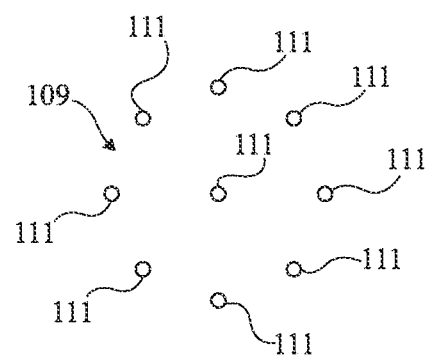
FIG. 2 is a front view schematically illustrating the arrangement of the pixels of an image sensor of the system of FIG. 1.

FIG. 2 is a front view of sensor 109 of FIG. 1, schematically illustrating the arrangement of pixels 111 on the sensor. In the shown example, sensor 109 comprises nine pixels 111 arranged in a same plane, eight of these pixels, which will be called peripheral pixels hereafter, being arranged in a circle, and the ninth pixel, which will be called central pixel hereafter, being at the center of the circle of peripheral pixels. In this example, the peripheral pixels are distributed in pairs, the pixels of a same pair being located at diametrically opposite points of the circle of peripheral pixels.

In the example of FIG. 1, sensor 109 is arranged so that the central pixel of the sensor is substantially located at focal point F of optical system 113.

Figure 3:
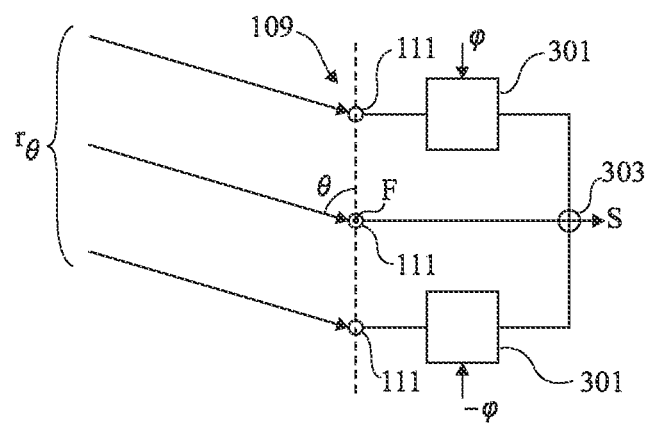
FIG. 3 is an enlarged cross-section view of a portion of the image acquisition system of FIG. 1, illustrating in further detail the operation of this system.

FIG. 3 is an enlarged cross-section view of a portion of the image acquisition system of FIG. 1, illustrating in further detail the operation of this system. FIG. 3 shows a diametrical line of three pixels 111 of sensor 109, comprising the central pixel and two peripheral diametrically opposite pixels of the sensor. Only considering radiation re reaching sensor 109 with an angle of incidence e relative to the diametrical pixel line, the sum of the signals received by the three pixels of FIG. 3 is equal to:

$$\left(1 + 2\cos\left(\frac{2\pi d \cos\theta}{\lambda}\right)\right) E_0 e^{j\omega t}$$

where $E_0$, $\theta$, $\lambda$, and $\omega$ respectively designate the amplitude, the angle of incidence, the wavelength and the pulse of radiation $r_\theta$, and where d designates the radius of the pixels circle, j designates the imaginary unit, and t designates time.

The absolute value of term $$K = 1 + 2\cos\left(\frac{2\pi d \cos\theta}{\lambda}\right)$$

varies according to the value of angle of incidence $\theta$. Thus, if it is considered that the three pixels of FIG. 3 form an elementary detection assembly providing an output signal equal to the sum of the signals received by the three pixels, this detection assembly intrinsically has a certain angular selectivity, that is, it is more sensitive to certain angles of incidence $\theta$ than to others. Such an angular selectivity particularly depends on the wavelength of the radiation and on interval d between neighboring pixels of the alignment.

FIGS. 4A to 4F are diagrams respectively showing, for different values of distance d between pixels of the pixel alignment of FIG. 3, the absolute value of term K according to angle of incidence $\theta$, for a wave having a frequency equal to 300 GHz ($\lambda$=1 mm in vacuum).

Figure 4A:
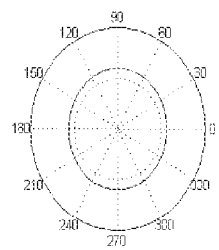
FIGS. 4A to 4F and 5 are diagrams illustrating an operating principle of the image acquisition system of FIGS. 1 to 3.
Figure 4B:
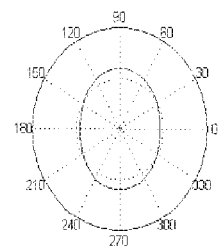
Figure 4C:
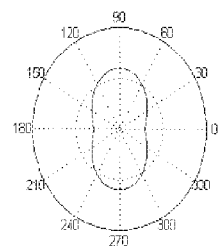
Figure 4D:
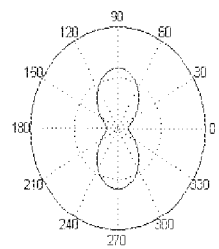
Figure 4E:
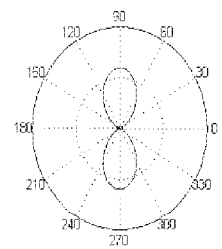
Figure 4F:
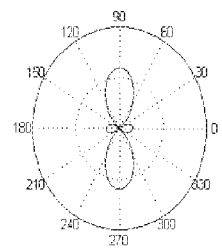

FIG. 4A shows the case where distance d is equal to 210 μm. In this case, it can be observed that the absolute value of term K is practically independent from angle $\theta$, that is, the intrinsic angular selectivity of the pixel alignment is relatively low.

FIGS. 4B to 4F show the cases where distance d is respectively equal to 420 μm, 630 μm, 840 μm, 1,050 μm, and 1,260 μm. Among these examples, the larger distance d, the larger the variations of the absolute value of term K according to angle $\theta$, and the higher the intrinsic angular selectivity of the pixel alignment. As an example, in FIG. 4F, it can be observed that when distance d is equal to 1,260 μm, the absolute value of term K is relatively high for angles $\theta$ close to 90 degrees, and practically zero for angles $\theta$ between 0 and 60 degrees and between 120 and 180 degrees. As a result, the detection assembly formed by the diametrical pixel line of FIG. 3 is relatively sensitive to waves arriving with an angle of incidence $\theta$ in the order of 90 degrees, and is little sensitive, or even insensitive, to waves arriving with angles of incidence $\theta$ ranging between 0 and 60 degrees and between 120 and 180 degrees.

In FIGS. 4A to 4F, it can be seen that, whatever distance d separating the pixels of the alignment, the intrinsic angular selectivity cone of the detection assembly is always centered on an angle of incidence $\theta$ equal to 90 degrees, that is, the rays which are best seen by the pixel alignment are those arriving with an angle of incidence $\theta$ equal to 90 degrees with respect to the alignment, that is, under normal incidence.

To modify angle of incidence $\theta$ best seen by the pixel alignment of FIG. 3, it may be provided, before adding the signals provided by the three pixels of the alignment, to phase-shift the signals provided by one or a plurality of the pixels of the alignment with respect to the signals provided by the other pixels of the alignment. As an example, it may be provided to shift the phase of the signals provided by the two diametrically opposite pixels of the alignment by respective phase-shift values ϕ and −ϕ with respect to the signals provided by the central pixel. For this purpose, in the image acquisition system of FIGS. 1 to 3, each peripheral pixel of the sensor may be connected to a phase-shift circuit 301 (FIG. 3) capable of shifting by a variable value the phase of the signals provided by the pixels. Further, each diametrical pixel line 111 may have an associated circuit 303 capable of providing a signal S representative of the sum of the signals respectively provided by the central pixel and by the diametrically opposite peripheral pixels in the line, after phase-shifting of the signals provided by the peripheral pixels by circuits 301. Sum S of the signals provided by the three pixels of the alignment after phase-shifting of the signals provided by the diametrically opposite pixels is provided by equation:

$$S = \left(1 + 2\cos\left(\frac{2\pi d\cos\theta}{\lambda} - \varphi\right)\right) E_0 e^{j\omega t}$$

Figure 5:
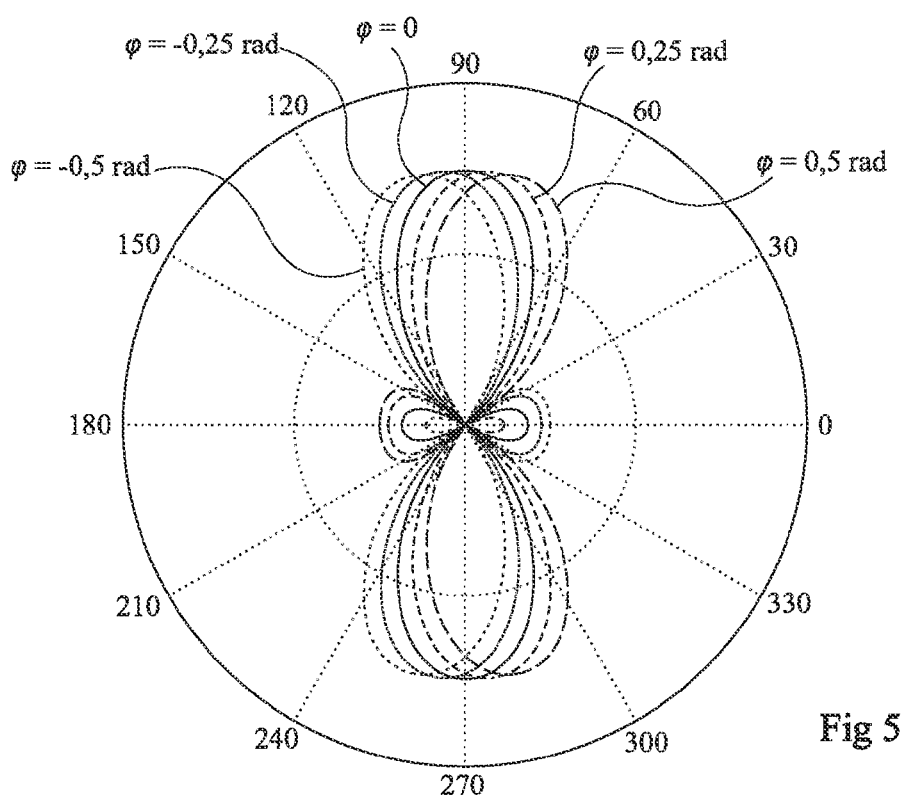

Varying term ϕ enables to control the orientation of the angular selectivity cone of the detection assembly formed by the pixel alignment of FIG. 3, and thus its best viewing angle (as illustrated in FIG. 5). This enables to achieve an angular filtering of the radiation reaching the pixel alignment of FIG. 3.

FIG. 5 is a diagram showing, for five different values of phase shift ϕ, the variation of the absolute value of term $$K' = 1 + 2\cos\left(\frac{2\pi d\cos\theta}{\lambda} - \varphi\right)$$

(or angular selectivity diagram) according to angle of incidence θ, for a wave having a frequency equal to 300 GHz and a distance d separating two neighboring pixels equal to 1,260 μm. For a zero phase shift ϕ, the angular selectivity diagram is identical to that of FIG. 4F, that is, the waves seen best by the pixel alignment of FIG. 3 are those arriving with an angle of incidence θ equal to 90 degrees. When phase shift ϕ varies, it can be observed that the main direction of the angular selectivity cone of the pixel alignment also varies. In this example, for phase shifts ϕ respectively equal to −0.5 rad, −0.25 rad, 0.25 rad, and 0.5 rad, the angles of incidence θ best seen by the pixel alignment are respectively equal to 1.95 rad (approximately 111.7 degrees), 1.76 rad (approximately 100.8 degrees), 1.38 rad (approximately 79.1 degrees), and 1.18 rad (approximately 67.6 degrees).

To acquire an image of scene 107, scene 107 may be illuminated by beam 105, and, while the scene is illuminated, the following steps may be implemented.

1) For each of the diametrical pixel lines of sensor 109, reading an output value representative of the power of signal S delivered by adder circuit 303 during a sensor integration period. During the integration period, phase shifts ϕ and −ϕ applied to the diametrically opposite pixels of the pixel lines remain constant and are for example the same for all diametrical lines of the sensor. The output values of the different diametrical lines of the sensor are for example read simultaneously; and 2) Repeating step 1) by changing, between two successive iterations, the value of phase-shifts ϕ and −ϕ applied to the diametrically opposite pixels of each diametrical line of the sensor.

An angular scanning of a plurality of portions of the scene is thus performed, which can enable to obtain an image of the scene having a greater resolution than the sensor. The resolution of the final image is conditioned by the incrementation or decrementation step of phase shift value ϕ, and by the number of diametrical pixel lines comprised in the sensor.

A disadvantage of the image acquisition system described in relation with FIGS. 1 to 5 is due to the fact that pixels 111 should be coherent pixels capable of providing output signals containing information relative to the incident radiation phase. For this purpose, a local oscillator (specific to each sensor pixel or common to all sensor pixels and connected by interconnection wires to all sensor pixels) providing a reference signal coherent with source 101 should be coupled with each sensor pixel. This results in relatively complex sensors having a significant electric power consumption.

It would be desirable to overcome all or part of these disadvantages. In particular, it would be desirable to have terahertz or infrared frequency image acquisition systems and methods enabling, without displacing the sensor, to obtain an image of a scene having a resolution greater than that of the sensor, compatible with pixels or detectors providing output signals which do not contain the incident radiation phase information.

After, a pixel capable of providing an output signal containing the incident radiation phase information will be called coherent pixel, and a pixel providing an output signal which does not contain the incident radiation phase information (for example, a photodiode) will be called non-coherent pixel.

Figure 6:
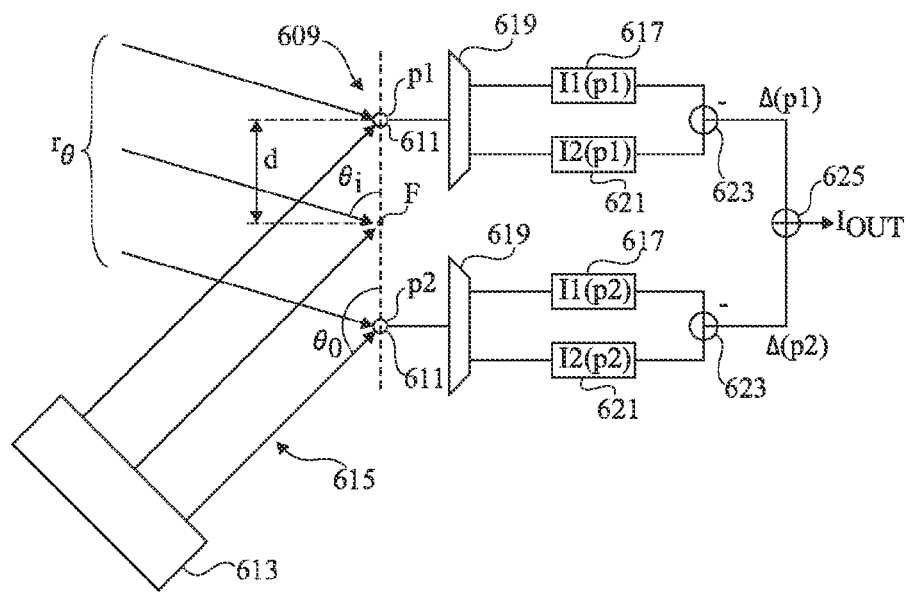
FIG. 6 is a cross-section view schematically and partially illustrating an embodiment of an active image acquisition system.

FIG. 6 is a cross-section view schematically and partially illustrating an embodiment of an active image acquisition system. The system of FIG. 6 comprises elements common with the image acquisition system described in relation with FIGS. 1 to 3. Such common elements have not been shown in FIG. 6 and will not be detailed hereafter. In particular, coherent electromagnetic wave emission source 101, which will be called main source hereafter, and optical system 113 are common to both systems and have not been shown in FIG. 6.

The image acquisition system of FIG. 6 comprises, instead of coherent image sensor 109 of the system of FIGS. 1 to 3, a non-coherent image sensor 609. Sensor 609 comprises a plurality of non-coherent detectors or pixels 611 sensitive to the waves emitted by source 101. In this example, sensor 609 comprises eight pixels 611 arranged in a same plane along a circle centered on the focal point of optical system 113, pixels 611 being arranged in pairs of diametrically opposite pixels. In this example, pixels 611 are capable of providing an output value proportional to the square of the module of the sum of the waves received during a pixel integration period. Pixels 611 are for example pixels of the type described in article "A broadband THz imager in a low-cost CMOS technology" by Schuster et al., or in article "A CMOS focal-plane array for terahertz imaging" by Pfeiffer et al. Another embodiment of a non-coherent terahertz pixel compatible with the image acquisition system of FIG. 6 will be described hereafter in relation with FIG. 8. More generally, the system of FIG. 6 is compatible with any type of non-coherent pixels, for example, a simple infrared photodiode in the case where source 101 emits infrared waves.

The image acquisition system of FIG. 6 further comprises a secondary source 613 emitting electromagnetic waves coherent with waves emitted by main source 101. In this example, source 613 is capable of emitting a secondary parallel beam 615, a planar wave coherent with the waves emitted by source 101. Source 613 is arranged so that, when it emits, beam 615 illuminates all the pixels of sensor 609 directly, that is, without passing through scene 107. In a preferred embodiment, sources 101 and 613 are confounded, and secondary beam 615 is generated by branching (via an optical system, not shown) part of the waves emitted by main source 101. This particularly enables to limit the electric consumption of the image acquisition system, and further enables to more easily ensure the coherence between the waves of main beam 105 and the waves of secondary beam 615. The described embodiments are however not limited to this specific case. As a variation, an image acquisition system where sources 101 and 613 are separate may be provided.

Considering, for simplification, that pixel 611 of sensor 609 receives an integral number n greater than 1 of planar waves of same pulse ω originating from n different points of scene 107 and reaching the pixel with different angles of incidence, the sum of the waves received by the pixel of these n points may be written as:

$$\sum_{0<i} U_i e^{j\omega t + \varphi_i}$$

where i is an integer from 1 to n, and where $U_i$ and $\phi_i$ designate the respective amplitudes and phases of the waves seen by the pixel.

The output signal of the pixel is proportional to the square of the module of the sum of the received waves, that is, after development, to:

$$\sum_{0<i} U_i^2 \sum_{0<i<k} 2U_i U_k \cos(\varphi_k - \varphi_i)$$

where k is an integer from 1 to n and different from i.

When secondary beam 615 of the acquisition system of FIG. 6 is present, the pixel further receives an additional planar wave of amplitude $U_0$ and of phase $\phi_0$. The signal delivered by the pixel is then proportional to:

$$\sum_{0<i} U_i^2 + \sum_{0<i<k} 2U_i U_k \cos(\varphi_k - \varphi_i) + \sum_{0<i} 2U_i U_0 \cos(\varphi_i - \varphi_0).$$

Difference Δ between signal I1 detected by the pixel in the presence of secondary beam 615 and signal I2 detected by the pixel in the absence of secondary beam 615 is proportional to term:

$$\sum_{0<i} 2U_i U_0 \cos(\varphi_i - \varphi_0).$$

Considering two diametrically opposite pixels p1 and p2 of the sensor, and calling $\phi_i^{p1}$ and $\phi_i^{p2}$ (with i varying from 1 to n) the phases of above-mentioned waves $U_i$ respectively seen by pixels p1 and p2, $\phi_0^{p1}$ and $\phi_0^{p2}$ the phases of above-mentioned wave $U_0$ respectively seen by pixels p1 and p2, and Δ(p1) and Δ(p2) the respective differences between signal I1 (p1) detected by pixel p1 in the presence of beam 615 and signal I2 (p1) detected by pixel p1 in the absence of beam 615, and between signal I1 (p2) detected by pixel p2 in the presence of beam 615 and signal I2 (p2) detected by pixel p2 in the absence of beam 615, sum $I_{OUT}$ of values Δ(p1) and Δ(p2) is proportional to term:

$$\sum_{0<i} 2U_i U_0 (\cos(\varphi_i^{p1} - \varphi_0^{p1}) + \cos(\varphi_i^{p2} - \varphi_0^{p2})).$$

Calling $\theta_i$ (i varying from 1 to n) the angles of incidence of above-mentioned waves $U_i$ relative to the line formed by pixels p1 and p2, terms $\phi_i^{p1}$, $\phi_i^{p2}$ may respectively be written as:

$$\varphi_i^{p1} = \phi + \frac{2\pi d \sin \theta_i}{\lambda} \text{ and } \varphi_i^{p2} = \phi - \frac{2\pi d \sin \theta_i}{\lambda},$$

where Φ is a constant term corresponding to the phase of all the waves incident on the focal plane of optical system 113, and where d is the radius of the sensor pixel circle. By working under Gauss's stigmatism conditions, where the rays form small angles with the focal axis, it can be observed that sum $I_{OUT}$ of intermediate values Δ(p1) and Δ(p2) is proportional to term:

$$\sum_{0<i} 4U_i U_0 \cos(\phi) \cos\left(\pi \frac{d}{\lambda}(\theta_i - \theta_0)\right)$$

Thus, considering that pixels p1 and p2 of FIG. 6 form an elementary detection assembly providing an output signal $I_{OUT}$ equal to the sum of values Δ(p1) and Δ(p2), this detection assembly intrinsically has a certain angular selectivity, that is, it is more sensitive to certain angles of incidence than to others. Such an angular selectivity depends not only on distance d and on wavelength λ of the considered radiation, but also on angle of incidence $\theta_0$ of secondary beam 615. In particular, the main direction of the angular selectivity cone, that is, the best viewing angle of the detection assembly, varies according to angle of incidence $\theta_0$ of secondary beam 615. More specifically, in this example, the best viewing angle of the detection assembly is equal to angle of incidence $\theta_0$ of secondary beam 615.

In this example, the image acquisition system comprises a device, not shown, enabling to mechanically vary angle $\theta_0$ of incidence of secondary beam 615 on sensor 609. As an example, the device may comprise a pivoting mirror and/or a pivoting lens, and an associated actuation system, for example comprising a motor.

To acquire an image of scene 107, scene 107 may be illuminated by beam 105, and, while the scene is illuminated, the following steps may be implemented by means of a control device, not shown.

1) For each of the diametrical pixel lines of sensor 609, reading, for each of the line pixels, a first pixel output value I1 at the end of a first pixel integration period during which secondary beam 615 is present. Output value I1 read for each pixel is for example stored in a memory 617 associated with the pixel, for example, via a multiplexer 619. Values I1 of all the sensor pixels are for example read simultaneously.

2) For each of the diametrical pixel lines of sensor 609, reading, for each of the line pixels, a second pixel output value I2 at the end of a second pixel integration period during which secondary beam 615 is absent (for example, by means of a shutter, not shown). Output value I2 read for each pixel is for example stored in a memory 621 associated with the pixel, for example, via a multiplexer 619. As an example, values I2 of all the sensor pixels are for example read simultaneously.

3) For each of the diametrical pixel lines of sensor 609, calculating, for each of the line pixels, an intermediate value Δ equal to the difference between output values I1 and I2 of the pixel read at steps 1) and 2). As an example, a subtraction circuit 623 is associated with each of the sensor pixels, this circuit receiving values I1 and I2 stored in memories 617 and 621 of the pixel, and delivering value Δ.

4) For each of the diametrical pixel lines of sensor 609, calculating an output value $I_{OUT}$ equal to the sum of the intermediate values Δ calculated for each of the line pixels. As an example, an adder circuit 625 is associated with each of the diametrical sensor pixel lines, such a circuit receiving the intermediate values Δ calculated by subtraction circuits 623 of the line, and delivering value $I_{OUT}$. Value $I_{OUT}$ calculated for each diametrical line of sensor pixels is representative of the intensity of the radiation transmitted by a point in the scene, and may be used to determine the value of a point of the final image.

5) Repeating steps 1) to 4) by changing, at each iteration, angle of incidence $\theta_0$ of secondary beam 615 on sensor 609.

An angular scanning of the scene is thus particularly easily carried out, and is capable of enabling to obtain an image of the scene having a greater resolution than the sensor. The resolution of the final image is conditioned by the incrementation or decrementation step of angle of incidence $\theta_0$ of beam 615 between two successive iterations, and by the number of diametrical pixel lines comprised in the sensor.

Figure 7:
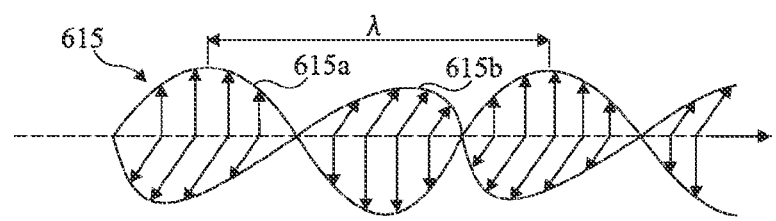
FIG. 7 schematically illustrates an operating principle of an alternative embodiment of the system of FIG. 6.

FIG. 7 illustrates an alternative embodiment of the image acquisition system of FIG. 6. In this alternative embodiment, angle of incidence $\theta_0$ of secondary beam 615 on sensor 609 is fixed, which especially enables to do away with a system of mechanical actuation of beam 615. In the example of FIG. 7, beam 615 comprises coherent parallel planar waves of same pulse ω 615a and 615b, polarized along different directions. In the shown example, waves 615a and 615b have crossed polarities, that is, orthogonal polarization directions. It is provided to place a polarizer (not shown) in front of each sensor pixel, the polarizers being selected so that, in each pair of diametrically opposite pixels of the sensor, one of the pixels receives from beam 615 waves 615a only, and the other pixel receives from beam 615 waves 615b only.

By varying the phase shift between waves 615a and 615b, an effect similar or identical to that obtained by varying angle of incidence $\theta_0$ of beam 615 in the image acquisition system described in relation with FIG. 6 is obtained. Thus, without modifying angle of incidence $\theta_0$ of beam 615, an angular scanning of the scene capable of enabling to obtain an image of the scene having a resolution greater than that of the sensor, can be performed. As an example, to acquire an image of scene 107, a method comprising steps 1) to 4) of the method described in relation with FIG. 6 may be implemented, where step 5) of the method described in relation with FIG. 6 is replaced with the following step.

5') Repeating steps 1) to 4) by changing, for each iteration, the phase shift between waves 615a and 615b of secondary beam 615.

The resolution of the final image is conditioned by the incrementation or decrementation step of the phase shift between waves 615a and 615b of beam 615, and by the number of diametrical pixel lines comprised in the sensor.

Figure 8:
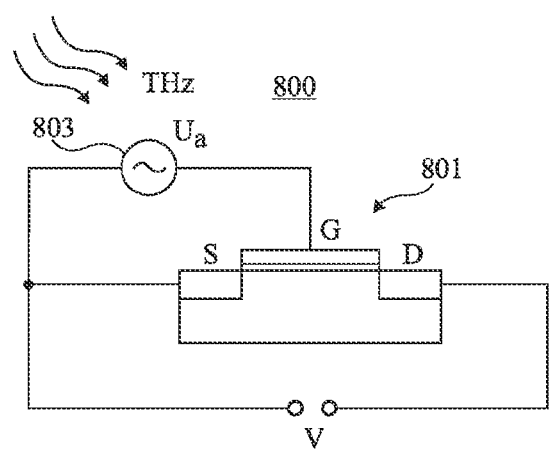
FIG. 8 is a cross-section view of an embodiment of a pixel of an image sensor of the system of FIG. 6.

FIG. 8 is a cross-section view of an embodiment of a non-coherent terahertz pixel 800 capable of being used in an image acquisition system of the type described in relation with FIGS. 6 and 7. In this example, pixel 800 comprises a MOS transistor 801, and an antenna 803 symbolized in the drawing by a terahertz signal generator. Antenna 803 is connected between the gate (G) and the source (S) of transistor 801. When a terahertz signal is received by the pixel, this signal is applied to the transistor in the form of a gate-source voltage, and the transistor provides, between its drain and its source, a D.C. output voltage V proportional to the envelope or amplitude of the incident terahertz radiation.

An advantage of the active image acquisition methods and systems described in relation with FIGS. 6 to 8 is that it is possible to obtain a high-definition image of a scene to be observed while using a sensor comprising a small number of pixels, and this, without displacing the sensor with respect to the scene. This enables to significantly limit the complexity, the cost, and the electric power consumption of the acquisition system with respect to known active image acquisition systems.

Another advantage of the image acquisition methods and systems described in relation with FIGS. 6 to 8 is that they are compatible with non-coherent pixels or detectors, which have the advantage of being simpler and less expensive than coherent pixels used in image acquisition systems of the type described in relation with FIGS. 1 to 5.

Specific embodiments have been described. Various alterations, modifications, and improvements will readily occur to those skilled in the art.

In particular, the described embodiments are not limited to the above-described examples of arrangement of the pixels on the sensor. It will be within the abilities of those skilled in the art to implement the desired operation while providing other pixel arrangements on the sensor. As an example, the sensor may comprise a plurality of concentric circles of pixels centered on the focal point of optical system 113. Further, the described embodiments are not limited to the example described in relation with FIGS. 6 and 7 where the sensor comprises eight pixels.

Further, the described embodiments are not limited to the above-described example where the waves illuminating the scene to be observed are seen by the sensor by transmission. The described embodiments are compatible with image acquisition systems where the waves emitted by the source are seen by the sensor by reflection on the scene.

Further, the described embodiments are not limited to terahertz or infrared image acquisition systems in the above-mentioned frequency range from 100 GHz to 100 THz. Other operating frequencies may be provided.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A method of acquiring an image of a scene illuminated by a first electromagnetic wave beam, by means of a sensor comprising at least two pixels sensitive to said first electromagnetic wave beam, comprising the steps of: a) for each pixel, reading a first output value of the pixel representative of the intensity of the radiation received by the pixel during a first integration period during which the sensor is illuminated by a second electromagnetic wave beam coherent with the first beam; and b) for each pixel, reading a second output value of the pixel representative of the intensity of the radiation received by the pixel during a second integration period during which the sensor is not illuminated by the second beam, wherein steps a) and b) are repeated a plurality of times by changing, between two successive iterations, the angle of incidence or a phase parameter of the second beam.

2. The method of claim 1, wherein, at each iteration, for each pixel of the sensor, a third value representative of the difference between the first and second output values of the pixel is calculated.

3. The method of claim 1, wherein the sensor comprises an even number of pixels arranged in a circle, the pixels of the circle being distributed in pairs at diametrically opposite points of the circle.

4. The method of claim 1, wherein, at each iteration, for each pixel of the sensor, a third value representative of the difference between the first and second output values of the pixel is calculated, wherein the sensor comprises an even number of pixels arranged in a circle, the pixels of the circle being distributed in pairs at diametrically opposite points of the circle, and wherein, at each iteration, for each pair of diametrically opposite pixels of the circle, a fourth value representative of the sum of the third values calculated for each of the pixels in the pair is calculated.

5. The method of claim 1, wherein the second beam comprises first waves polarized along a first direction, and second waves polarized along a second direction different from the first direction.

6. The method of claim 5, wherein the first and second directions are orthogonal.

7. The method of claim 5, wherein, at each iteration, a value of the phase shift between the first waves and the second waves is modified.

8. The method of claim 1, wherein said electromagnetic waves are at a frequency in the range from 100 GHz to 100 THz.

9. The method of claim 1, wherein the pixels are non-coherent pixels.

10. The method of claim 1, wherein the second beam results from a branching of the first beam.

11. A system for acquiring an image of a scene, comprising: a source emitting a first electromagnetic wave beam capable of illuminating the scene; a sensor comprising at least two pixels sensitive to said first electromagnetic wave beam; a source emitting a second electromagnetic wave beam coherent with the first beam capable of illuminating the sensor; and a control device capable of implementing the steps of: a) for each pixel, reading a first output value of the pixel representative of the intensity of the radiation received by the pixel during a first integration period during which the sensor is illuminated by the second beam; and b) for each pixel, reading a second output value of the pixel representative of the intensity of the radiation received by the pixel during a second integration period during which the sensor is not illuminated by the second beam, and repeating steps a) and b) a plurality of times by changing, between two successive iterations, the angle of incidence or a phase parameter of the second beam.

* * * * *